United States Patent [19]

Bergquist et al.

[11] Patent Number: 4,569,932

[45] Date of Patent: Feb. 11, 1986

[54] LOW TOXICITY RADIATION SENSITIZER

[75] Inventors: Barton L. Bergquist; James C. Chang, both of Cedar Falls, Iowa

[73] Assignee: University of Northern Iowa Foundations, Cedar Falls, Iowa

[21] Appl. No.: 586,311

[22] Filed: Mar. 5, 1984

Related U.S. Application Data

[62] Division of Ser. No. 440,840, Nov. 12, 1982, Pat. No. 4,490,543.

[51] Int. Cl.$^4$ ............................................. A61K 31/155
[52] U.S. Cl. .................................................... 514/185
[58] Field of Search .......................... 424/245; 514/185

[56] References Cited

PUBLICATIONS

Chemical Abstracts 94:40620z (1981).

*Primary Examiner*—Leonard Schenkman
*Attorney, Agent, or Firm*—Zarley, McKee, Thomte, Voorhees & Sease

[57] ABSTRACT

This invention relates to cisplatin type fluorescently labeled compounds. In particular, the compounds are bis (5-aminofluorescein)-dichloroplatinum (II) or certain substituted analogues thereof. The compounds are useful as radiation sensitivity enhancers and as fluorescent biological tracers. The invention also relates to a unique, single step synthesis for preparing said compounds.

4 Claims, 3 Drawing Figures

LOW TOXICITY RADIATION SENSITIZER

CROSS REFERENCE TO RELATED APPLICATION

This application is a division of application Ser. No. 440,840, filed Nov. 12, 1982 now U.S. Pat. No. 4,490,543 issued Dec. 25, 1984.

BACKGROUND OF THE INVENTION

In addition to being used in cancer chemotherapy, cisplatin is also known as a radiation sensitizer. That is, such that the cisplatin enhances the effect of ionizing radiation on malignant tumors in order to improve local and regional cancer treatment by radiation, see, for example, Overgaard, et al., Cancer Treatment Reports Vol. 65, Nos. 5-6, May/June, 1981, p. 501–503, which is incorporated herein by reference. There, it is reported that cisplatin will enhance the radiation response in tumors by a factor of between 1.2 and 1.7 time the effectiveness if no cisplatin is used. The report goes on to describe the use of cisplatin as a marked and selective enhancement of radiation's effects in solid tumors. Cisplatin has the formula:

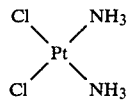

The chemical name for cisplatin is cis-diaminedichloroplatinum(II). It is a square planar molecule and its effectiveness in biological systems is believed to be related to its configuration. The compound was recognized for its biological significance in the 1960's and its radiation sensitizing properties were demonstrated in the mid-1970's.

While cisplatin per se has been known as an effective radiation sensitizer, it does have problems which have inhibited its practical use. The primary problem is its high level of toxicity to normal living cells. Thus, while it may successfully sensitize a carcinoma, making it highly susceptible to radiation treatment, it also is quite toxic to the surrounding normal cells. There is, therefore, a real and continuing need to develop a radiation sensitizer which is at least equally as effective as cisplatin with respect to the enhancement of sensitivity of carcinomas to radiation, but which will allow such sensitization without being toxic to surrounding normal living cells.

Needless to say, if one could develop a radiation sensitizer of high level sensitizing effect, but with minimal toxicity to surrounding normal living cells, the net effect would be that smaller doses of radiation could be used to give the effect now achieved with only larger radiation doses and thus, the total body exposure to radiation reduced. Alternatively, for a given radiation dose, its effectiveness could be increased without fear of causing high level toxicity to surrounding normal tissue cells.

It is a primary objective of the present invention to provide a radiation sensitizer which is at least equal to cisplatin in selective enhancement of radiation response, but which provides such radiation response with a much, much lower toxicity level to normal live cells.

An additional objective of the present invention is to provide a radiation sensitizer which is at least equal to cisplatin in enhancement of radiation response, but which is several times less toxic than cisplatin to normal living cells.

A further objective of this invention is to provide a radiation sensitizer which is at least equal to cisplatin in radiation sensitization effect, but which is estimated to be up to ten times less toxic to normal cells.

Another object is to provide a compound which like cisplatin itself has antineoplastic properties.

A still further objective of the present invention is to provide a molecular tracer which is fluorescent, thus providing a unique and highly effective biological tracer which is capable of binding to DNA nucleotides, proteins, and lipids.

Yet another objective of this invention is to provide a fluorescent biological tracer which also will function as an effective biological stain for use in electron microscopy and fluorescence microscopy.

Still another objective of the present invention is to provide a radiation sensitizer that has stability and solubility properties which make the compounds easy to administer in dosage quantity.

And another objective of the present invention is to provide a radiation sensitizer which is soluble in water and soluble in common universal solvents such as dimethylsulfoxide, methyl alcohol, ethyl alcohol, acetone, etc.

Another very important objective of the present invention is to provide a highly effective, single step synthesis for production of fluorescently labeled cisplatin type compounds, which do not employ cisplatin at all in the synthesis procedure, but instead employ readily available compounds in a single step, direct combination synthesis.

The method and manner of accomplishing each of the above objectives, as well as others, will become apparent from the detailed description of the invention which follows hereinafter.

SUMMARY OF THE INVENTION

This invention relates to cisplatin type fluorescently labeled compounds which are effective radiation sensitizers. In particular, the compounds are bis(5-aminofluorescein)dichloroplatinum(II) (abbreviated cis-CFP) or certain substituted analogs thereof. They are equal to cisplatin from the standpoint of their radiation sensitivity enhancement, but are up to ten times less toxic to normal living cells than cisplatin. In addition, the compounds are highly effective, fluorescent biological tracers. The invention also relates to a unique, single step synthesis for preparing fluorescently labeled cisplatin type compounds, without ever employing cisplatin in the synthesis route. As a result, the synthesis involves a platinum salt and a relatively non-toxic 5-aminofluorescein, which are readily available.

BRIEF DESCRIPTION OF THE DRAWINGS

The drawings are graphs illustrating the good radiation sensitizing properties of the compounds of this invention, coupled with their low toxicity level compared to cisplatin.

DETAILED DESCRIPTION OF THE INVENTION

Figure 1:
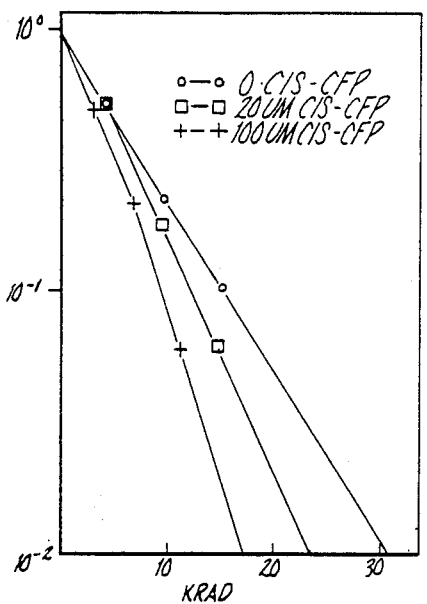

The compounds of this invention have the following formula:

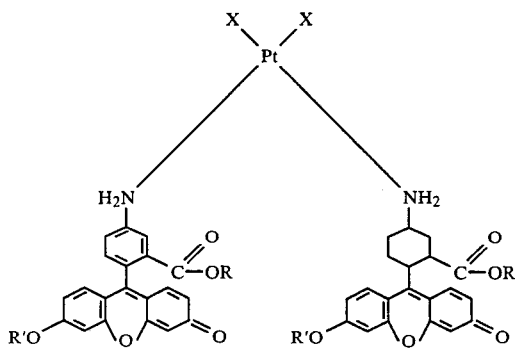

wherein "X" is a halide and R and R' are selected from the group consisting of hydrogen, $C_1$ to $C_{12}$ alkyl, $C_1$ to $C_{12}$ alkenyl, $C_1$ to $C_{12}$ alkynyl, and aryl. Preferably "X" is a chloride or bromide, and most preferably chloride. It is preferred that R and R' be selected from the group consisting of $C_1$ to $C_6$ alkyl, alkenyl, alkynyl, and aryl. Most preferably, both R and R' are hydrogen.

The very most preferred compound of the invention is bis(5-aminofluorescein)dichloroplatinum(II).

The compounds of the present invention can be thought of as fluorescein derivatives of cisplatin.

Cisplatin has been known for several decades but has only become biologically important since about the mid-1960's. It is a square planar molecule known to have adverse properties to normal, but especially to neoplastic cells. It is also known as an effective radiation sensitizer. The term "radiation sensitizer" refers to enhancement of the effect of ionizing radiation on cells, most typically malignant cells in order to improve local and regional cancer treatments. Cisplatin selectively sensitizers and enhances the effective radiation response in malignant growths with a lesser effect in normal tissues. Thus, cisplatin has been accorded some high level interest, because of its potential use in chemotherapy. However, one primary disadvantage with cisplatin is that it has a high level of toxicity to normal tissue cells.

Surprisingly, and contrary to the expectations in working with cisplatin per se, the fluorescein derivatives of this invention are equal to cisplatin as radiation sensitizers, but, contrary to cisplatin, have a very low level toxicity to surrounding tissue cells. In fact, data developed to date, reveal a toxicity level up to as much as ten times lower than cisplatin. As a result, the compounds of this invention, and particularly the most preferred compound bis(5-aminofluorescein)dichloroplatinum(II), can be used as a much more effective radiation sensitizer than cisplatin. In particular, since the aminofluorescein derivative has a low toxicity level, larger quantities can be used in dosage treatments. As a result, successful radiation treatments can occur with much smaller radiation doses, resulting in overall reduced body exposure to radiation. Then too, large doses of the radiation sensitizer can be used, increasing the radiation sensitization effect, without any significant worry of the high level toxicity to normal cells. In particular, toxicity levels of the most preferred compound of this invention are up to ten times less than cisplatin.

The compounds of the present invention are also useful as biological tracers, since they are both fluorescent and have high binding capabilities to nucleic acids, proteins and lipids. Prior to the development of the compounds of this invention, it is not believed that there has been a biological tracer which is both fluorescent and also offers binding properties similar to that of cisplatin in that it may bind to nucleic acids, proteins and lipids, and thus be easily traceable. This fluorescent property, coupled with the binding ability to biologically important compounds, allows for fluorescent labeling of cells in biological work.

While the compounds discussed have been referred to as platinum compounds, it is possible that other compounds can be made employing as the metal atom, any of the metals of the platinum metal series, that is, rubidium, rhodium, palladium, osmium, irridium, and platinum. It is therefore contemplated as still within the scope of this invention if the central metal atom of the platinum compounds is replaced with other of the referred to metals of the platinum metal series.

Another highly important feature and advantage of the compounds of the present invention is that they have stability and solubility characteristics which make them easy to work with from the standpoint of dosage units. That is to say, they are soluble in water, they are relatively stable, and they will dissolve in many universally employed solvents such as dimethylsulfoxide, methanol, ethanol and acetone.

A surprisingly simple and straightforward single step reaction synthesis has been developed for producing the compounds of this invention. The method is surprising because one would normally except cisplatin per se to be the starting material, since the compounds are derivatives of cisplatin. However, cisplatin is not involved in the reaction at all. And yet, the compound which is produced has all of the radiation sensitivity properties of cisplatin. In accordance with the process of this invention, 5-aminofluorescein (Isomer I), or a substituted 5-aminofluorescein, is reacted with an alkali metal tetrachloroplatinate(II) in a single step, direct combination synthesis. 5-aminofluorescein (Isomer I) has the formula:

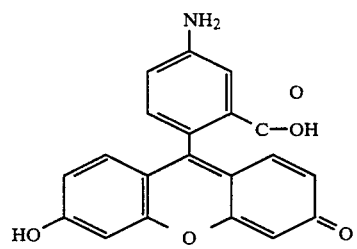

The alkali metal tetrachloroplatinate(II) is preferably potassium tetrachloroplatinate(II) of the formula $K_2[PtCl_4]$. In the preferred methodology, an aqueous solution of potassium tetrachloroplatinate(II) is mixed with a hot methanol solution of 5-aminofluorescein, with the molar ratio of potassium tetrachloroplatinate(II) to 5-aminofluorescein being 1:2. The solutions are mixed and the mixture is heated (with evaporation) at a slightly elevated temperature, perhaps 60° C. After cooling to room temperature, a brown precipitate forms which can be separated and recrystallized.

The following examples are offered to further illustrate, but not limit, the invention. It is understood that modifications may be made in the illustrated examples.

EXAMPLES

Preparation of bis(5-aminofluorescein)dichloroplatinum(II) was accomplished using direct combination of an aqueous solution of potassium tetrachloroplatinate(II) and 5-aminofluorescein. In particular 0.415 grams of $K_2[PtCl_4]$ in 25 milliliters of water was added to 0.694 grams of 5-aminofluorescein in 50 milliliters of boiling methanol. They were mixed, and the solution was kept at about 60° C. for one hour. Thereafter, it was allowed to cool, at which point a brown precipitate was observed. The precipitating compound was filtered, washing a little with absolute ethanol, and then with diethyl ether. The brown compound remained. It weighed 0.4 grams.

The reaction process was run again, exactly as described above, and gave a brown solid of 0.5 grams.

Nuclear magnetics resonance (NMR) testing, infrared (IR) analysis, visible-UV spectroscopy, and quantitative, elemental analysis all confirmed the presence of bis(5-aminofluorescein)dichloroplatinum(II). In these runs, the starting platinum compound came from the Alpha Division of Ventron Corporation, and the starting 5-aminofluorescein compound came from Sigma Chemical in St. Louis, Mo. Of course, other convenient and suitable sources for the starting materials may be utilized.

Numerous repetitions of the synthesis procedure shown here, have occurred and all upon various analysis techniques mentioned herein confirm the presence of bis 5-aminofluorescein)dichloroplatinum(II).

The process was repeated using as the starting material $K_2[PtBr_4]$ and the resulting product was bis(5-aminofluorescein)dibromoplatinum(II).

The bis(5-aminofluorescein)dichloroplatinum(II) prepared in the manner previously described herein, was tested for effectiveness as a radiation sensitizer. In particular, the compound was complexed with nucleotides in vitro. The stability of the compound was studied in a buffered saline solution over a period of time. Finally, the cell growth effects of the compound from the standpoint of its effects on living cells were studied, as described below.

The drawings illustrate the effective nature of the compounds of this invention as radiation sensitizers, and compare the toxicity level of the compounds of this invention with the toxicity level of cisplatin from the standpoint of their effects on living cells.

FIG. 1 shows the effectiveness of the compound of this invention, in particular bis(5-aminofluorescein)dichloroplatinum(II) in terms of its effectiveness as a radiation sensitizer. In particular, in looking at FIG. 1, the "x" axis shows radiation dose as measured in kilorads (krad). The "y" axis shows the surviving fraction of bacterial cells (S. typhimurium Tm 677). The line represented by black dots and dashes shows the effect of radiation alone on this bacterial system under a nitrogen blanket. This simulates anaerobic conditions in vivo. The lines showing squares with dashes and pulses with dashes shows the decrease in survival produced by 20 um and 100 um cis-CFP respectively over a range of radiation dosages. The radiosensitization produced by cis-CFP exhibits a dose dependent effect. It also exhibits a much reduced toxicity as compared to equamolar concentrations of cisplatin; this makes it difficult to make direct comparisons. Studies using the S. typhimurium Tm 677 bacterial system produce the following data.

TABLE 1

| | Concentration of Compound | Toxicity after ½ hour at room temperature [no radiation survival] | Radiation Enhancement Ratio |
| --- | --- | --- | --- |
| Cisplatin | 100 uM | 10% | 2.4 |
| cis-CFP | 100 uM | 100% survival | 1.6 |

Even though the enhancement of the 100 uM concentration is less for cis-CFP than for displatin, the extreme differences in toxicity demonstrate the utility of cis-CFP as compared to cisplatin.

Though difficult to compare directly, other work using mice to study cisplatin-induced radiosensitization shows a radiation enhancement ratio of up to 1.7. This is comparable to the 1.6 value demonstrated for cis-CFP in the bacterial system.

Also, cisplatin under nitrogen is an assay using E. coli exposed to $5 \times 10^{-5}M$ cisplatin shows an enhancement ratio of about 1.77. It therefore can be seen that although direct comparision is difficult, they are comparable in radiation sensitizing ability.

Figure 2:
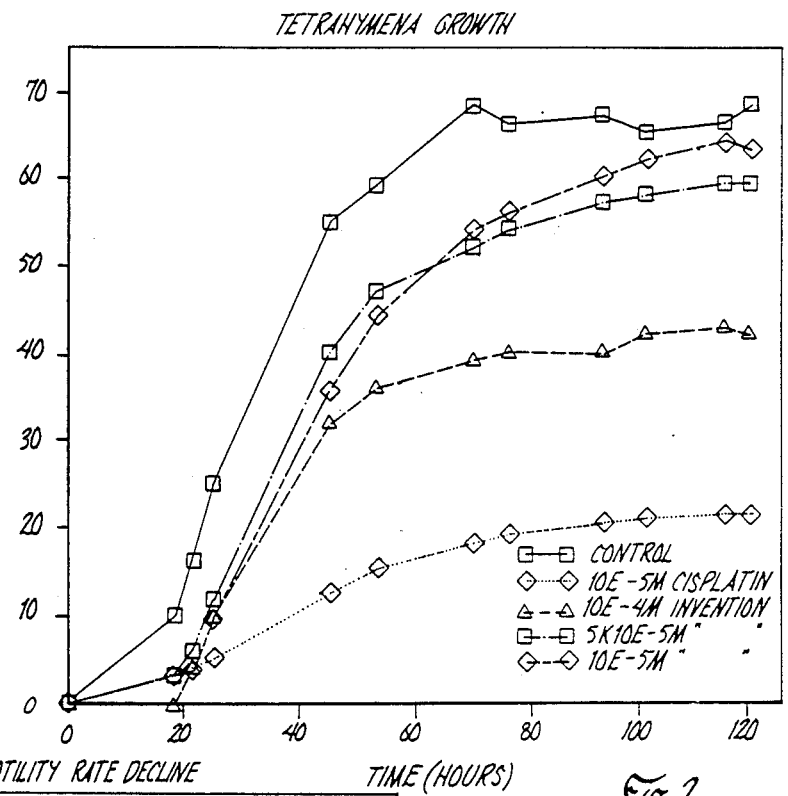

FIG. 2 shows the growth of a culture of Tetrahymena in a nutrient medium which comprises 2% by weight of proteose peptone, 0.1% by weight sodium hydrogen phosphate, 0.1% sodium acetate and with the balance being distilled water. The "x" axis shows culture growth in time with the "y" axis indicating media density, an indication of cell numbers. As can be seen, the greatest cell growth is exhibited in the control, which are free living and growing protozoan cells in the presence of a nutrient. The toxicity of cisplatin when added to the control solution at a concentration of $10^{-5}$ molar is also shown. The toxicity of the compounds of this invention at $10^{-4}$ molar and $10^{-5}$ molar concentrations are likewise shown. It can be seen that the level of toxicity compounds of the present invention is much, much less at a given molar concentration than is cisplatin. This is further illustrated in FIG. 3, which shows the same free living protozoan cell Tetrahymena, but shows the motility rate declining in the presence of cisplatin and a compound of the invention. Cisplatin is the dotted line and the compound of the invention is the solid line. There, the "x" axis measures time of exposure with the "y" axis measuring the motility rate of the organisms. The steeper the line indicating the mobility of the organism, the more toxic the compound. There, the concentration in both instances of cisplatin and the compound of the invention was $2 \times 10^{-3}$ molar. It can be seen that at any given time, the mobility is much more reduced by cisplatin than the compound of this invention, indicating a much higher toxicity level of cisplatin.

Figure 3:
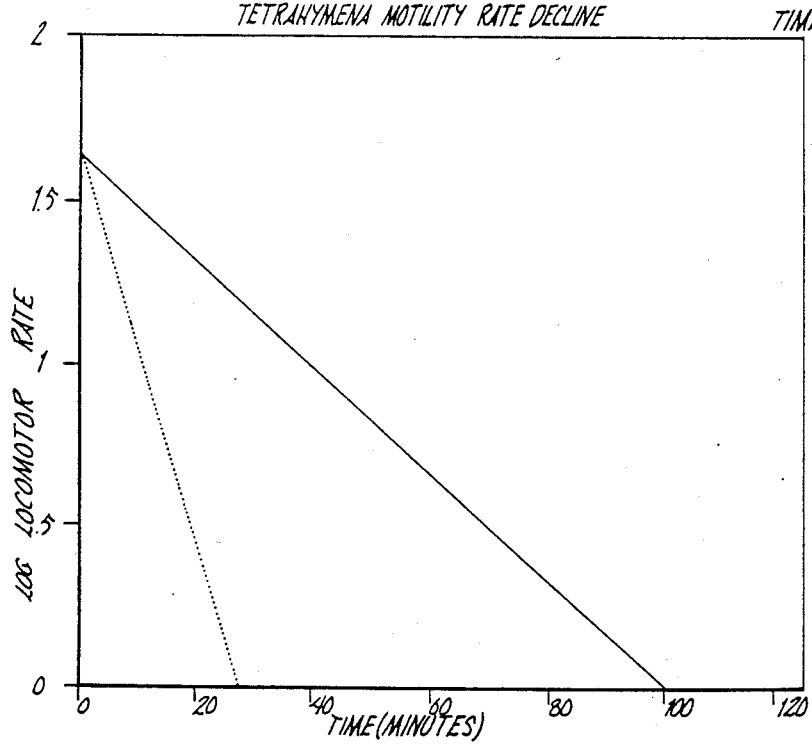

It therefore can be seen that the compounds of the present invention are substantially equal in radiation sensitizing effect to cisplatin, but that they are up to as many as ten times less toxic to normal living cells, see FIGS. 2 and 3 and the data presented therein.

Thus, the invention accomplishes at least all of its stated objectives.

What is claimed is:

1. A method of increasing the radiation sensitivity of living cells comprising:
   administering to an animal a small radiation sensitizing effective amount of a compound of the formula

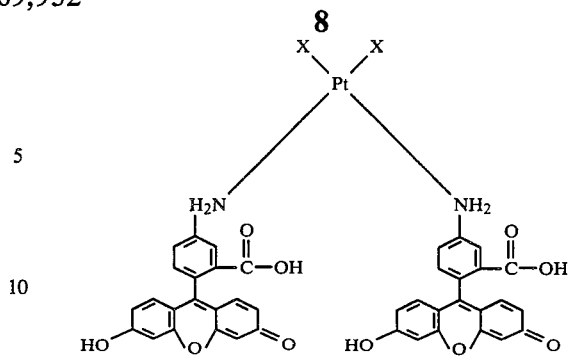
where X is a halide.
2. The method of claim 1 wherein X is chloride.
3. The method of claim 1 wherein X is bromide.
4. The method of claim 1 wherein the amount of said compound administered is from about 20 micromoles to about 100 micromoles.
* * * * *